United States Patent [19]

Anton et al.

[11] Patent Number: 4,803,272

[45] Date of Patent: Feb. 7, 1989

[54] S-MODIFIED ADENOSYL-1,8-DIAMINO-3-THIOOCTANE DERIVATIVES

[75] Inventors: David L. Anton; Bruce D. Korant; Chia-Lin J. Wang, all of Wilmington, Del.

[73] Assignee: E. I. Du Pont de Nemours and Company, Wilmington, Del.

[21] Appl. No.: 17,889

[22] Filed: Feb. 24, 1987

[51] Int. Cl.$^4$ .................... A61K 31/52; C07D 473/34
[52] U.S. Cl. .................................... 544/277; 514/261; 514/266
[58] Field of Search ................ 544/262, 277; 514/261, 514/266

[56] References Cited

U.S. PATENT DOCUMENTS

| | | | |
|---|---|---|---|
| 4,221,794 | 9/1980 | Simon | 514/261 |
| 4,230,708 | 10/1980 | De Clerq | 514/261 |
| 4,362,729 | 12/1982 | Vince | 514/261 |
| 4,376,116 | 3/1983 | Coward et al. | 514/46 |
| 4,543,255 | 9/1985 | Shealy | 514/258 |
| 4,649,140 | 3/1987 | Schaeffer | 544/277 |

OTHER PUBLICATIONS

Beauchamp, (1985), J. Med. Chem., 28, pp. 982–987.
Sunkara et al., Science, 219:851 (1983).

Primary Examiner—Donald G. Daus
Assistant Examiner—Mark W. Noel

[57] ABSTRACT

S-Modified Adenosyl-1,8-Diamino-3-Thiooctane derivatives which are useful as interferon potentiators and polyamine biosynthesis inhibitors are disclosed.

4 Claims, No Drawings

S-MODIFIED ADENOSYL-1,8-DIAMINO-3-THIOOCTANE DERIVATIVES

BACKGROUND OF THE INVENTION

1. Field of the Invention

This invention relates to compounds which are useful as interferon potentiators and polyamine biosynthesis inhibitors.

2. Background of the Invention

Interferon is a protein which exhibits antitumor and antiviral as well as a wide range of other biological activities. The advent of recombinant DNA technology has permitted the production of large quantities of interferon for a variety of therapeutic applications, including antitumor and antiviral treatments. The synthesis of polyamines, such as putrescine, spermidine and spermine, is important in cellular replication. In biological systems, these polyamines are synthesized by spermidine synthase and spermine synthase. Potentiators of interferon antitumor and antiviral activity and inhibitors spermidine synthase are of interest to the medical field.

U.S. Pat. No. 4,376,116 discloses a compound having the formula

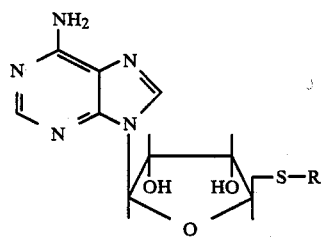

wherein
R is
CH—(CH$_2$)$_5$NHR'
(CH$_2$)$_2$—NH$_2$ wherein R' is hydrogen or aminopropyl and salts thereof. The compounds are said to be specific inhibitors for enzyme catalyzed alkyl transfer reactions involving the enzymes spermidine synthase and spermine synthase. The reference also discloses methods for treating cystic fibrosis and subjects having a parasitic infection.

Sunkara et al., *Science*, 219:851 (1983) discloses tumor suppression with a combination of α-difluoromethyl ornithine (DFMO) with interferon. The reference discloses that DFMO is an irreversible inhibitor of othnithine decarboxylase, the first step in polyamine synthesis. The reference further discloses that DFMO in combination with interferon gave total or near total suppression of tumor growth of B16 melanoma cells.

SUMMARY OF THE INVENTION

The present invention provides a compound of formula (I)

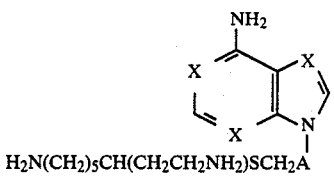

H$_2$N(CH$_2$)$_5$CH(CH$_2$CH$_2$NH$_2$)SCH$_2$A wherein X is independently CH or N, and A is selected from the group consisting of —CH$_2$OCH$_2$—, —CH$_2$-CHOHCHOHCH$_2$—, and

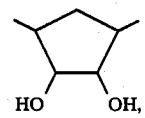

and salts thereof. The invention also provides an improvement in the use of interferon for antitumor or antiviral treatments. The improvement comprises contacting interferon with compound of formula (I). The invention further provides a method of inhibiting the activity of spermidine synthase comprising contacting spermidine synthase with the compound of formula (I). In addition, the invention provides a pharmaceutical composition comprising an amount of the compound of formula (I) effective for potentiating interferon in antitumor or antiviral treatments and a pharmaceutically acceptable carrier.

DETAILED DESCRIPTION OF THE INVENTION

The present invention resides in compounds of formula (I) which are useful as interferon potentiators and spermidine synthase inhibitors. The interferon potentiating activity of the specified compounds makes them useful in antitumor and antiviral therapeutic applications. The ability of the specified compounds to inhibit spermidine synthase makes them useful as anti-parasitic agents. The latter activity also makes the specified compounds useful in biochemical research where inhibition of spermidine synthase is desired.

Compounds of formula (I) can be prepared by any convenient method employing starting materials wherein positions 1, 3, and 7 of the fused ring structure are independently C or N. These materials are known in the art. In a preferred method, 9-[2-oxa-5-thia-6-(2-aminoethyl)-11-aminoundecyl]-6-amino-purine is prepared by reacting the sodium salt of 6-chloropurine with 1,3-dioxalane to produce 9-[2-oxa-4-hydroxybutyl]-6-chloropurine which is the aminated in the presence of liquid ammonia to give 9-[2-oxa-4-hydroxybutyl]-6-aminopurine. The hydroxyl group of the latter compound is then converted to a chloro group by interaction with thionyl chloride. The resulting chloro compound is then reacted with 1,8-diazido-3-(thioacetyl)octane in the presence of sodium hydroxide to give 9-[2-oxa-5-thia-6-(2-azidoethyl)-11-azidoundecyl]-6-aminopurine which is then reduced in the presence of triphenylphosphine and ammonium hydroxide to give the 9-[2-oxa-5-thia-6-(2-aminoethyl)-11-aminoundecyl]-6-amino-purine.

In a preferred method, 9-[2,3-dihydroxy-6- thia-7-(2-aminoethyl)-12-amino-dodecyl]-6-aminopurine is prepared by converting cis-3,4-dihydroxy-trans-5-hydroxymethylbutyrolactone to 1-phenyl-2-oxa-5,6-dihydroxy-7-(9-adenyl)heptane. The hydroxyl groups of the latter compound are protected by interaction with triethylorthoformate followed by cleavage of the benzyl group with lithium metal in liquid ammonia. The formed hydroxyl group is the mesylated and treated with 1,8-diazido-3-(thioacetyl)octane in the presence of sodium hydroxide followed by reduction with hydrogen in the presence of palladium to produce the 9-[2,3-dihydroxy-6-thia-7-(2-aminoethyl)-12-amino-dodecyl]-6-aminopurine.

In a preferred method, t-adenyl-2,c-3,c-dihydroxy-4,t[2-thia-3-(2-aminoethyl)-8-aminooctyl]-cyclopentane hydrochloride is prepared by converting 2-azabicyclo[2.2.1]hept-5-ene-3-one to [±]2,t-hydroxymethyl-4,t-[9-adenyl]-6,8-dioxa-7-ethoxy-cisbicyclo[3.3.0]octane which was mesylated followed by reaction with 1,8-diazido-3-(thioacetyl)octane in the presence of sodium hydroxide followed by reduction with hydrogen in the presence of palladium to produce the t-adenyl-2,c-3,c-dihydroxy-4,t[2-thia-3-(2-aminoethyl)-8-aminoocty-1]cyclopentane hydrochloride.

The present invention is further described by the following examples wherein all parts and percentages are by weight and degrees are Celcius unless otherwise stated. Interferon potentiating and spermidine synthase inhibiting activities of the present compounds were determined according to the following general procedures.

Interferon Potentiating Activity

The assay procedure employed for interferon potentiation was a modification of a procedure used for determining interferon antiviral activity. Specified animal cells were cultured in monolayers on plastic or in suspensions using a stirred vessel. Normal [diploid]cells or transformed [immortalized]cells, such as WISH [Hela]-cells, were used with equivalent results.

In order to assay the quantity of biologically active interferon in a test sample, selected cells were exposed for 2 to 24 hours to culture medium into which interferon had been added. Usually, the interferon was added at several dilutions, each dilution to a separate cell sample, so that a dose-response curve could be generated by the cells. After a selected time interval [the interferon may have been left on the cells, but was usually removed], and a challenge dose of a virus was added to all the cells. The dose, usually in the range of 0.1 infectious unit per cell, was chosen to give a lethal cytopathic effect in 24-36 hours. At the point of maximum lethality [on control cells, not treated with interferon, as determined visually under a microscope], the medium was removed, and all cells remaining attached were fixed and stained with 0.1% crystal violet in 50% ethanol. End points of the titration [defined as that dilution of interferon where 50% of the cells remain attached]were determined visually.

In the case of the concomitant assay of an interferon potentiator, the test compound was added, at one particular concentration, to a dilution series of interferons. Usually the test compound was added with the interferon, but it could also be added prior to adding interferon. The potentiating effect was then determined at the conclusion of the antiviral assay and was reflected in the 50% protection level having shifted to a greater dilution of interferon, compared to the absence of the compound.

Spermidine Synthase Inhibiting Activity

The assays for spermidine synthase inhibition contained: 100 mM Tris.HCl, 2 mN putrescine, 20 μM decarboylated S-adenosyl-L-methionine 8000 cpm [2-14C]decarboxylated S-adenosyl-L-methionine [adjusted to a pH of 8.2]in a final volume of 50 μL. Reactions were initiated by the addition of enzyme and incubated for 10 minues at 37° . The reactions were stopped by the additions of 5 μL of 100 mM spermidine and 5 μL of a slurry of 160 mg/mL of Darco G60 in water. The mixtures were centrifuged at 10,000×g for 2 minutes and a 40 μL aliquot of the supernate counted. Blank reactions were run using zero incubation time, or omitting enzyme or putrescine.

This assay made use of the adsorption of unreacted substrate, decarboxylated S-adenosyl-L-methionine, on charcoal while leaving the product polyamine in solution.

EXAMPLE 1

Preparation of 9-[2-Oxa-5-thia-6-(2-aminoethyl)-11aminoundecyl]-6-Aminopurine

A. 9-[2-Oxa-4-hydroxybutyl]-6-chlorpurine

A solution of the sodium salt of 6-chloropurine was generated by reacting of one gram of 6-chloropurine and 290 mg of sodium hydride in 10 mL of DMF at 0° for 30 minutes and then at ambient temperature for one hour. To the solution [at −60°]was added a pretreated [−78°, 15 minutes]mixture of 1,3-dioxalane [1.59 g]and iodotrimethylsilane [3.15 mL]in cyclohexene [distilled, 25 mL]. The resulting reaction mixture was then stirred at ambient temperature for two hours. The solvent was removed and 10% aqueous potassium fluoride solution and saturated sodium bicarbonate were added. The resulting mixture was extracted with $CHCl_3$ three times. The $CHCl_3$ layer was washed with saturated sodium bisulfite and dried over sodium sulfate. Removal of the solvent gave 820 mg of 9-[2-oxa-4-hydroxybutyl]6-chloropurine as a solid. NMR [$d_6$-DMSO]: δ8.70 [d, 1H], 8.62 [d, 1H], 5.65 [d, 2H], 4.20 [bs, 1H], 3.50 [m, 4H].

B. 9-[2-Oxa-4-hydroxybutyl]-6-aminopurine

A mixture of 9-[2-oxa-4-hydroxybutyl]-6-chloropurine [4.4 g, 19 mmol]prepared in Part A and 400 mL of methanol containing liquid ammonia [100 mL]was heated at 95° in a steel bomb for 16 hours. Ammonia was allowed to evaporate and the mixture was filtered. The filtrate was concentrated in vacuo and solid was formed upon addition of methanol. The solid was collected to give 2.78 g of 9-[2-oxa-4-hydroxybutyl]-6-aminopurine. NMR [$d_6$-DMSO]: 8.23 [s, 1H], 8.13 [s, 1H], 7.20 [bs, 2H], 5.50 [s, 2H], 3.43 [m, 4H]; Ms: m/z 209.0903 [M+], calculated for $C_8H_{11}N_5O_2$: 209.0912.

C. 9-[2-Oxa-4-chlorobutyl]-6-aminopurine

To a solution of 9-[2-oxa-4-hydroxybutyl]-6-aminopurine prepared in Part B [0.76 g, 3.63 mmol]in HMPA [8 mL] was added thionyl chloride [1 mL]. The resulting mixture was stirred at ambient temperature for one hour before it was poured into ice water. The pH was adjusted to 9 with concentrated ammonium hydroxide and solid was formed. The solid was collected and washed with water and ether to give 535 mg of 9-[2-oxa-4-chlorobutyl]-6-aminopurine. NMR [$d_6$-

DMSO]: 8.27 [s, 1H], 8.17 [s, 1H], 7.23 [bs, 2H], 5.59 [s, 2H], 3.75 [m, 4H].

D. 9-[2-Oxa-5-thia-6-(2-azidoethyl)-11-azidoundecyl]-6-aminopurine

A mixture of 9-[2-oxa-4-chlorobutyl]-6aminopurine [500 mg, 2.19 mmol] prepared in Part C and 1.8-diazido-3-[thioacetyl]octane [890 mg, 3.29 mmol] in DMSO [15 mL]and 4N sodium hydroxide solution [3 mL] was stirred at room temperature for two hours. The resulting mixture was poured into water and extracted with chloroform three times. The combined chloroform layer was washed with saturated sodium chloride and dried over sodium sulfate. The crude product was purified by flash column chromatography to give 370 mg of 9-[2-oxa-5-thia-6-(2-azidoethyl)-11-azidoundecyl]-6-aminopurine as a white solid, m.p. 140°–142° C.; IR [nujol]: 2100 cm$^{-1}$; NMR [CDCl$_3$]: δ8.43 [s, 1H, 8.00 [s, 1H], 5.80 [bs, 2H], 3.73 [t, J=7 Hz, 2H], 3.45 [m, 4H], 2.67 [m, 3H], 2.00–1.25 [m, 10H]; Ms: m/z 224.0587 [M+—C$_8$H$_{15}$N$_6$], calculated for C$_8$H$_{10}$N$_5$OS: 224.0606.

E. 9-[2-Oxa-5-thia-6-(2-aminoethyl)-11-aminoundecyl]-6-aminopurine

A solution of 9-[2-oxa-5-thia-6-(2-azidoethyl)-11-azidoundecyl]-6-aminopurine prepared in Part D [40 mg, 0.095 mmol] and triphenylphosphine [82 mg, 0.31 mmol]in pyridine [0.5 mL] was stirred at ambient temperature for 3.5 hours. Concentrated ammonium hydroxide [3 drops] was added and the resulting reaction mixture was stirred for two hours at ambient temperature. The solvent was removed in vacuo and the resulting residue was dissolved in 10% HCl and extracted with ether twice. The separated aqueous layer was basified with concentrated ammonium hydroxide and extracted with chloroform three times. The combined chloroform layer was dried over sodium sulfate. Removal of the solvent gave 19 mg of 9-[2- oxa-5-thia-6-(2-aminoethyl)-11-aminoundecyl]-6-aminopurine as a white solid. NMR [CD$_3$OD]: δ8.33 [s, 1H], 8.23 [s, 1H], 5.70 [s, 2H], 3.76 [t, J=7 Hz, 2H], 3.25–2.50 [m, 7H], 2.00–1.30 [m, 10H]: Ms: m/z 224.0609 [M+—C$_8$H$_{19}$N$_2$], calculated for C$_8$H$_{10}$N$_5$OS: 224.0606.

F. Activity of 9-[2-Oxa-5-thio-6-(2-aminoethyl)-11-aminoundecyl]-6-aminopurine Interferon potentiating activity and spermidine synthase inhibiting activity of the 9-[2-oxa-5-thia-6-(2-aminoethyl)-11-aminoundecyl]-6-aminopurine prepared in this Example were determined according to the General Procedures described above.

The challenge virus was vesicular stomatitis virus [VSV], New Jersey strain. Activity was assayed on Maden-Darby bovine kidney cells in monolayer cultures. It was determined that the title compound at a concentration of 12.5 micrograms/mL gave a 2× potentiation of human alpha [leucocyte] interferon. A concentration of 50 micrograms/ml of the title compound gave an 8× potentiation of human beta interferon and a 4× potentiation of human gamma interferon. The compound by itself showed no antiviral activity against VSV.

A concentration of 50 micrograms/ml of the title compound on MDBK [bovine, transformed] and WISH [human, transformed] cells gave an 8× potentiation of human alpha interferon. The same concentration on EBTr [bovine, normal] cells gave a 6× potentiation of human alpha interferon.

A concentration of 100 micrograms/ml of the title compound on poliomyelitis gave a 16× potentiation of human beta interferon. The same concentration on Vesicular Stomatitis gave a 32× potentiation of human beta interferon.

It was also determined that about 0.1 mM of the specified compound was needed to effect 50% inhibition of spermidine synthase activity.

EXAMPLE 2

Preparation of 9-[2,3-dihydroxy-6-thia-7-(2-aminoethyl)-12-aminododecyl]-6-aminopurine

A. 2-Hydroxymethyl-3,6,8-trioxa-4-oxo-7,7-dimethyl bicyclo[3.3.0] octane

A mixture of c-3,4-dihydroxy-t-5-hydroxymethyl-butyrolactone [25 g, 0.169 mol] and 2,2-dimethoxypropane [30 mL, 0.25 mol] in acetone [100 mL] containing camphorsulfonic acid [2 g] was stirred at ambient temperature for 68 hours. The solvert was removed, the resulting residue was diluted with methylene chloride, washed with saturated sodium bicarbonate, saturated sodium chloride, and dried over magnesium sulfate. Removal of the solvent gave the crude product which was purified by high performance liquid chromatography to afford 19 g of 2-hydroxymethyl-3,6,8-trioxa-4-oxo-7,7-dimethyl bicyclo[3.3.0]octane. NMR [CDCl$_3$]: δ4.83 [m, 2H], 4.51 [t, 1H], 3.90 [m, 2H], 2.67 [m, 1H], 1.47 [s, 3H], 1.37 [s, 3H].

B. 2-[2-Oxa-3-phenyl propyl]-3,6,8-trioxa-4-oxo-7,7-dimethyl bicyclo[3.3.0]octane A mixture of 2-hydroxymethyl-3,6,8-trioxa4-oxo-7,7-dimethyl bicyclo[3.3.0]octane [100 mg, 0.53 mmol] prepared in Part A and benzyl bromide [91 mg, 0.53 mmol] in glyme [3 mL] containing sodium hydride [59.6% oil dispersion, 26 mg, 0.65 mmol] was stirred at ambient temperature for about 18 hours. The resulting mixture was then poured into a mixture of saturated ammonium chloride and ice. The aqueous layer was extracted with ether and the ether layer was dried over magnesium sulfate. Removal of the solvent afforded 86 mg of 2-[2-oxa-3-phenyl propyl]-3,6,8-trioxa-4-oxo-7,7-dimethyl bicyclo[3.3.0]octane which was used directly for the next reaction.

C. 2,2-Dimethyl-4-[1-hydroxy-3-oxa-4-phenylbutyl]-5-hydroxymethyl-1,3-dioxacyclopentane A suspension of 2-[2-oxa-3-phenyl propyl]-3,6,8-tri-oxa-4-oxo-7,7-dimethyl bicyclo[3.3.0]octane [86 mg, 0.3 mmol] prepared in Part B and lithium aluminum hydride [12 mg, 0.3 mmol] in ether [3 mL] was stirred at 0° for one hour. The resulting mixture was then quenched sequentially with water [0.3 mL], 15% aqueous sodium hydroxide [0.3 mL], and water [1 mL]. The resulting mixture was stirred at ambient temperature for 30 minutes and then dried over sodium sulfate. Filtration followed by removal of the solvent gave the crude product which was purified on preparative thin layer plates to yield 47 mg of 2,2-dimethyl-4-[1-hydroxy-3-oxa-4-phenyl butyl]-5-hydroxymethyl-1,3-dioxacyclopentane, m.p. 33° C.; IR [nujol]3250 cm$^{-1}$; NMR [CDCl$_3$]: δ7.32

[s, 5H], 4.57 [s, 2H], 4.50–3.50 [m, 7H], 3.20 [bs, 2H, —OH], 1.33 [2s, 6H].

D. 2,2-Dimethyl-4-[1-hydroxy-3-oxa-4-phenyl butyl]-5-[3,3-diphenyl-3-t-butyl-2-oxa-3-silapropyl]-1,3-dioxacyclopentane A mixture of 2,2-dimethyl-4-[1-hydroxy-3-oxa-4-phenyl butyl]-5-hydroxymethyl-1,3-dioxacyclopene [1 g, 3.54 mmol] prepared in Part C, tertbutyldiphenylchlorosilane [1.04 g, 3.72 mmol] and imidazole [290 mg, 4.25 mmol] in DMF [5 mL] was stirred at ambient temperature for five hours. The resulting mixture was then diluted with ether, washed with water and dried [MgSO4]. The crude product was purified by flash column chromatography to give 1.8 g [98%] of 2,2-dimethyl-4-[1-hydroxy-3-oxa-4-phenyl butyl]-5-[3,3-diphenyl-3-t-butyl-2-oxa-3-silapropyl]-1,3-dioxacyclopentane. NMR [CDCl3]: δ7.75–7.33 [m, 15H], 4.64 [s, 2H], 4.50–3.50 [m, 7H], 1.33 [s, 6H], 1.11 [s, 9H].

E. 2,2-Dimethyl-4-[1-(S-methyl dithiocarbonyl)-3-oxa-4-phenyl butyl]-5-[3,3-diphenyl-3-t-butyl2oxa-3-silapropyl]-1,3-dioxacyclopentane A mixture of 2,2-dimethyl-4-[1-hydroxy-3-oxa-4-phenyl butyl]-5-[3,3-diphenyl-3-t-butyl-2-oxa-3-silapropyl]-1,3-dioxacyclopentane [1.8 g, 3.46 mmol] prepared in Part D in THF [15 mL] containing sodium hydride [59.6% oil dispersion, 280 mg, 6.92 mmol] and imidazole [5 mg] was stirred at ambient temperature for two hours. Carbon disulfide [0.65 mL] was then added and one hour later, methyl iodide [0.6 g] was added. The resulting reaction mixture was stirred for another 15 minues and it was diluted with ether, washed with saturated ammonium chloride, saturated sodium chloride and dried [MgSO4]. The crude product was purified by flash column chromatography to give 725 mg of 2,2-dimethyl-4-[1-(S-methyl dithiocarbonyl)-3-oxa-4-phenyl butyl]-5-[3,3-diphenyl-3-t-butyl-2-oxa-3-silapropyl]-1,3-dioxacyclopentane. NMR [CDCl3]: δ7.75–7.15 [m, 15H], 5.80 [m, 1H], 4.60–3.50 [m, 6H], 4.50 [s, 2H], 2.43 [s, 3H], 1.43 [s, 3H], 1.37 [s, 3H], 1.07 [s,9H].

F. 2,2-Dimethyl-4-[3-oxa-4-phenyl butyl]-5-[3,3-diphenyl-3-t-butyl-2-oxa-3-silapropyl}-1,3-dioxacyclopentane.

A solution of 2,2-dimethyl-4-[1-(S-methyl dithiocarbonyl)-3-oxa-4-phenyl butyl]-5-[3,3-diphenyl-3-t-butyl-2-oxa-3-silapropyl]-1,3-dioxacyclopentane [0.7 g, 1.14 mmol] prepared in Part E in toluene [10 ml] containing tri-n-butyltin hydride [0.4 ml, 1.4 mmol] was refluxed for about 18 hours. The solvent was removed and the resulting residue was purified by flash column chromatography to give 510 mg of 2,2-Dimethyl-4-[3-oxa-4-phenyl butyl]-5-[3,3-diphenyl-3-t-butyl-2-oxa-3-silapropyl]-1,3-dioxacyclopentane. NMR [CDCl3]: δ7.75–7.15 [m, 15 H], 4.53 [s, 2H], 4.50–3.50 [m, 6H], 1.98 [m, 2H], 1.40 [s, 3H], 1.36 [s, 3H], 1.07 [s, 9H].

G. 2,2-Dimethyl-4-[3-oxa-4-phenyl butyl]5-hydroxymethyl-1,3-dioxacyclopentane A solution of 2,2-dimethyl-4-[3-oxa-4-phenyl butyl]-5-[3,3-diphenyl-3-t-butyl-2-oxa-3-silapropyl]-1,3-dioxacyclopentane [490 mg, 0.97 mmol] prepared in Part F in THF [5 mL] was treated with tetra-n-butylammonium fluoride [1M in THF, 3 mL] at ambient temperature for two hours. The solvent was removed and the resulting residue was diluted with ether, washed with saturated sodium chloride and dried [MgSO4]. The crude product was purified by flash column chromatography to give 204 mg of 2,2-dimethyl-4-[3-oxa-4-phenyl butyl]-5-hydroxymethyl-1,3-dioxacyclopentane. NMR [CDCl3]: δ7.33 [s, 5H], 4.52 [s, 2H], 4.30–4.00 [m, 2H], 3.60 [t, 4H], 2.18 [t, 1H, —OH], 1.86 [dt, 2H], 1.43 [s, 3H], 1.33 [s, 3H].

H. 1-Phenyl-2-oxa-5,6-dihydroxyheptyl methylsulfonate

A solution of 2,2-dimethyl-4-[3-oxa-4-phenyl butyl]-5-hydroxymethyl-1,3-dioxacyclopentane [100 mg, 0.35 mmol] prepared in Part G in methylene chloride [3 mL] containing triethylamine [0.2 mL] and mesyl chloride [48 mg,0.42 mmol] was stirred at 0° for one hour. The resulting mixture was then diluted with ether, washed with saturated sodium bicarbonate, saturated sodium chloride, and dried [MgSO4]. Removal of the solvent gave the crude compound which was dissolved in methanol [2 mL] and treated with p-toluenesulfonic acid at ambient temperature for about 18 hours. Methanol was removed, the residue was diluted with ether and washed with saturated sodium chloride. Removal of the solvent after drying over sodium sulfate gave 87 mg of 1-phenyl-2-oxa-5,6-dihydroxyheptyl methylsulfonate.

I. 1-Phenyl-2-oxa-5,6-dihydroxy-7-(9-adenyl)heptane

A mixture of adenine [215 mg, 1.5 mmol] and sodium hydride [59.6% oil dispersion, 55 mg, 1.35 mmol] in DMF [2 mL] was heated at 50° for one hour. Then a solution of 1-phenyl-2-oxa-5,6-dihydroxyheptyl methylsulfonate [100 mg, 0.3 mmol] in DMF [1 mL] was added and the mixture was heated at 90° for three hours. The solvent was removed, ethanol was added and the resulting solid was filtered off. Removal of ethanol gave the crude product which was purified by flash column chromatography to afford 37 mg of 1-phenyl-2-oxa-5,6-dihydroxy-7-(9-adenyl)heptane. NMR [CD3OD]: δ8.23 [s, 1H], 8.10 [s, 1H], 7.33 [s, 5H], 4.50 [s, 2H], 4.70–3.50 [m, 6H], 2.25–1.50 [m, 2H].

J. 2-Ethoxy-4-[3-oxa-4-phenyl butyl]-5-(9-adenyl)methyl-1,3-dioxacyclopentane A solution of 1-phenyl-2-oxa-5,6-dihydroxy-7-(9-adenyl)heptane [160 mg, 0.47 mmol] prepared in Part I in triethylorthoformate [5 mL] containing concentrated hydrochloric acid [0.5 mL] was stirred at ambient temperature for about 18 hours. The resulting mixture was quenched with 50% aqueous sodium hydroxide to pH 8. Triethylorthoformate was taken up with hot chloroform and water. The then removed in vacuo, the resulting residue was separated aqueous layer was extracted twice with hot chloroform and the combined chloroform layer was dried [Na2SO4]. Removal of the solvent gave 171 mg of 2-ethoxy-4-[3-oxa-4-phenyl butyl]-5-(9-adenyl)methyl-1,3-dioxacyclopentane.

K. 2-Ethoxy-4-[2-hydroxyethyl]-5-(9-adenyl)methyl1,3-dioxacyclopentane

Small pieces of lithium wire [55 mg, 7.85 mmol] were added to 10 mL of liquid ammonia [distilled over sodium metal]. The deep blue solution was stirred at −33° for 30 minutes and then a solution of 2-ethoxy-4-[3-oxa-4-phenyl butyl]-5-(9-adenyl)methyl-1,3-dioxacyclopentane [237 mg, 0.59 mmol] prepared in Part J in THF [2 mL] was added. The resulting mixture was stirred at −33° for two hours before quenching with solid ammonium chloride. Liquid ammonia was allowed to evaporate and the resulting residue was dissolved in water and extracted with hot chloroform three times. The combined chloroform layer was dried over sodium sulfate. Removal of the solvent gave the crude product which was purified by flash column chromatography to afford 42 mg of 2-ethoxy-4-[2-hydroxyethyl]-5-(9-adenyl)methyl-1,3-dioxacycloentane. NMR [CD$_3$OD]: δ8.25–7.90 [4s, 2H], 5.97, 5.80 [2s, 1H], 4.70–3.45 [m, 8H], 1.90 [t, 2H], 1.33–1.00 [m, 3H].

L.
2-Ethoxy-4-[3-thia-4-(2-azidoethyl)-9-azidononyl]-5-(9-adenyl)methyl-1,3-dioxacyclopentane A solution of 2-ethoxy-4-[2-hydroxyethyl]-5-(9-adenyl)methyl-1,3-dioxacyclopentane [100 mg, 0.31 mmol] prepared in Part K in pyridine [3 mL] was mixed with mesyl chloride [53 mg, 0.46 mmol] at ambient temperature for two hours. Pyridine was removed and the resulting residue was diluted with saturated sodium chloride solution and extracted three times with chloroform. Removal of the solvent after drying [Na$_2$SO$_4$] afforded 138 mg of the mesylate which was dissolved in DMSO [2 mL] and treated with 1,8-diazido-3-[thioacetyl]octane [124 mg, 0.46 mol] in the presence of 4N aqueous sodium hydroxide solution [1 mL]. The resulting mixture was stirred at ambient temperature for two hours, then poured into water and extracted three times with chloroform. The combined chloroform layer was washed with saturated sodium chloride and dried [Na$_2$SO$_4$]. The crude product was purified by flash column chromatography to give 79 mg of 2-ethoxy-4-[3-thia-4-(2-azidoethyl)-9-azidononyl]-5-(9-adenyl)methyl-1,3-dioxacyclopentane. IR [CH$_2$Cl$_2$]: 2090, 1625 cm$^{-1}$; NMR [CDCl$_3$]: δ8.33 [s, 1H], 7.93 [2s, 1H], 6.18 [s, 2H], 5.92, 5.80 [2s, 1H], 4.75–1.00 [m, 28H]; HRMS m/z 324.1143 [M$^+$—C$_8$H$_{15}$N$_6$], calculated for C$_{13}$H$_{18}$N$_5$O$_3$S, 324.1130.

M.
9-[2,3-Dihydroxy-6-thia-7-(2-aminoethyl)-12-aminoethyl)-12-aminododecyl]-6-aminopurine hydrochloride A mixture of 2-ethoxy-4-[3-thia-4-(2-azidoethyl-9-azidononyl]-5-(9-adenyl)methyl-1,3-dioxa cyclopentane [100 mg, 0.19 mmol] prepared in Part L in methanol [5 mL] containing 10% Pd/C [50 mg] was stirred under hydrogen overnight. The resulting mixture was treated with 2 mL of 10% aqueous hydrochloric acid at 50° for three hours. Removal of the solvent afforded 74 mg of 9-[2,3-dihydroxy-6-thia-7-(2-aminoethyl)-12-aminoethyl)-12-aminododecyl]-6-aminopurine hydrochloride. NMR [CD$_3$OD]: δ8.50 [s, 1H], 8.43 [s, 1H]; 4.50–1.00 [m, 23H].

L. Activity of 9-[2,3-Dihydroxy-6-thia-7-(2-aminoethyl)-12-aminoethyl)-12-aminododecyl]-6-aminopurine hydrochloride Spermidine synthase inhibiting activity of the 9-[2,3-dihydroxy-6-thia-7-(2-aminoethyl)-12-aminododecyl]-6-aminopurine prepared in this Example was determined according to the General Procedures described above. It was found that 0.02 mM of the specified compound was needed to effect 50% inhibition of spermidine synthase.

EXAMPLE 3
Preparation of t-Adenyl-2,c-3,c-dihydroxy-4,t[2-thia-3-(2-aminoethyl)-8-aminooctyl] cyclopentane hydrochloride

A.
Exo-cis-5,6-Dihydroxy-2-azabicylo[2.2.1]heptan-3-one

A mixture of 2-azabicyclo[2.2.1]hept-5-ene-3-one [100 mg, 0.9 mmol], N-methylmorpholine-N-oxide [112 mg, 0.95 mmol] and a catalytic amount of osmium tetroxide [one crystal] in acetone-water [5:1] was stirred at ambient temperature for 36 hours. Sodium bisulfite [100 mg], hydrous magnesium silicate [1.2 g] and water [8 mL] were added and the resulting mixture was stirred for one hour. The mixture was filtered, the solvent was evaporated and the crude product was purified by flash column chromatography to afford 98 mg of exo-cis-5,6-dihydroxy-2-azabicyclo[2.2.1]heptan-3-one.

B. Methyl 4,c-aminohydrochloride-2,t-3,t-dihydroxycyclopentanecarboxylate

Exo-cis-5,6-dihydroxy-2-azabicyclo[2.2.1]heptan-3-one prepared in Part A was converted to methyl 4,c-aminohydrochloride-2,t-3,t-dihydroxycyclopentanecarboxylate by the procedure reported in J. Org. Chem., 46, 3268 (1981), the disclosure of which is incorporated herein by reference. The specifed starting material [10 g, 6.669 mmol] was refluxed in 3N aqueous HCl [50 ml] for 3 hours followed by rotary evaporation to dryness. The resulting residue was then refluxed in 1N methanolic HCl [60 ml] for 2 hours, and the resulting solution was rotary evaporated to dryness to yield 13.5 g of methyl 4,c-aminohydrochloride-2,t-3,t-dihydroxycyclopentanecarboxylate.

C. Methyl 4,c-[t-butylcarbamoate]-2,t-3,t-dihydroxycyclopentanecarboxylate

A solution of methyl 4,c-aminohydrochloride-2,t-3,t-dihydroxycyclopentanecarboxylate [13.16 g, 62.2 mmol] prepared in Part B in 10% aqueous dioxane [200 mL] was treated with BOC-ON [30.6 g, 124.4 mmol] in the presence of triethylamine [27 mL, 195 mmol] at ambient temperature for about 12 hours. The solvent was removed in vacuo and the resulting residue was purified by flash column chromatography to yield 12 g of methyl 4,c-[t-butylcarbamoate]-2,t-3,t-dihydroxycyclopentanecarboxylate. NMR [CDCl$_3$]: δ5.00 [bs, 1H], 4.26 [m, 1H], 3.90 [m, 2H], 3.73 [s, 3H], 2.90 [m, 1H], 2.45 [m, 1H], 1.73 [m, 1H], 1.43 [s, 9H].

D.
2,t-Methyloxycarbonyl-4,t-[t-butylcarbamoate]-6,8-dioxa-7,7-dimethyl-cis-bicyclo[3.3.0]octane The methyl 4,c-[t-butylcarbamoate]-2,t-3,t-dihydroxycyclopentanecarboxylate [8.58 g, 31.1 mmol] prepared in Part C was contacted with 2,2-dimethoxypropane [5 mL] in acetone [25 mL] in the presence of a catalytic amount of camphorsulfonic acid [100 mg] at ambient temperature for 45 minutes. The solvent was removed and the resulting residue was diluted with chloroform, washed with saturated sodium bicarbonate, saturated sodium chloride and dried [MgSO$_4$]. The crude product was purified by flash column chromatography to give 5.6 g of 2,t-methyloxycarbonyl-4,t-[t-butylcarbamoate]-6,8-dioxa-7,7-dimethyl-cis-bicyclo[3.3.0]octane. NMR

[CDCl₃]: δ5.26 [m, 1H], 4.87 [d, 1H], 4.47 [d, 1H], 4.03 [m, 1H], 3.73 [s, 3H], 3.10–1.75 [m, 3H], 1.47 [s, 9H], 1.30 [s, 6H].

E. 2,t-Hydroxymethyl-4,t-[t-butylcarbamoate-6,8-dioxa-7,7-dimethyl-cis-bicyclo[3.3.0]octane A solution of 2,t-methyloxycarbonyl-4,t-[t-butylcarbamoate]-6,8-dioxa-7,7-dimethyl-cisbicyclo[3.3.0]octane [7.87 g, 24.9 mmol] prepared in Part D in ether [15 mL] was added to a suspension of lithium aluminum hydride [1.13 g, 29.9 mmol] in ether [50 mL] at 0°. The resulting mixture was stirred at 0° for one hour and then quenched with water [1 mL], 15% aqueous sodium hydroxide [1 mL], and again water [3.4 mL]. The mixture was stirred at ambient temperature for 30 minutes. Filtration followed by evaporation of the solvent in vacuo gave the curde product [6.69 g] which was purified by flash column chromatography to afford pure 2,t-hydroxymethyl-4,t-[t-butylcarbamoate]-6,8-dioxa-7,7-dimethyl-cisbicyclo[3.3.0]octane. NMR [CDCl₃]: δ5.40 [m, 1H], 4.60–3.60 [m, 4H], 2.50–1.50 [m, 3H], 1.47 [s, 12H], 1.30 [s, 3H].

F. 4,t-Aminohydrochloride-2,c-3,c-dihydroxycyclopentanemethanol

A mixture of 2,t-hydroxymethyl-4,t-[t-butylcarbamoate]-6,8-dioxa-7,7-dimethyl-cis-bicyclo[3.3.0]octane [115 mg, 0.4 mmol] prepared in Part E in THF - 10% aqueous hydrochloric acid [3 mL-3 mL] was heated at 50° for one hour. Removal of the solvent gave 74 mg of 4,t-aminohydrochloride-2,c-3,c-dihydroxycyclopentanemethanol. NMR [CD₃OD]: δ 4.00–3.50 [m, 5H], 2.50–1.25 [m, 3H].

G. [±]-4,t-[5-Amino-6-chloro-4-pyrimidinylamino]2,c-3,c-dihydroxycyclopentanemethanol 4,t-aminohydrochloride-2,c-3,c-dihydroxycyclopentanemethanol prepared in Part F was converted to [±]-4,t-[5-amino-6-chloro-4-pyrimidinylamino]-2,c-3,c-dihydroxycyclopentanemethanol by the procedure reported in J. Am. Chem. Soc., 91, 3075 [1969], the disclosure of which is incorporated herein by reference. A solution containing 3.7 g [20.16 mmol] of the specified starting material, 4.96 g of 5-amino-4,6-dichloropyrimidine, 8.4 mL of triethylamine, and 50 mL of 1-butanol was heated under reflux for 80 hours. The solvent was removed in vacuo. The resulting residue was dissolved in H₂O and washed with methylene chloride. Removal of the water gave the title product which was used without purification for the next step.

H. [±]2,t-Hydroxymethyl-4,t-[6-chloro-9H-9-yl]-6,8-dioxa-7-ethoxy-cis-bicyclo[3.3.0]octane A mixture of 6.65 g of the [±]-4,t-[5-amino-6-chloro-4-pyrimidinyl-amino]-2,c-3,c-dihydroxycyclopentanemethanol prepared in Part G, 80 mL of triethyl orthoformate, and 2.5 mL of 12N HCl was stirred at ambient temperature for 24 hours. The solvent was removed in vacuo and the residue was basified to pH 9 with concentrated ammonium hydroxide. The aqueous layer was extracted with hot chloroform and the resulting chloroform layer was dried (Na₂SO₄) The resulting crude product was purified by flash column chromatography to give 1.187 g of [±]-2,t-hydroxymethyl-4,t-[6-chloro-9H-purin-9-yl]-6,8-dioxa-7-ethoxy-cis-bicyclo[3.3.0]octane.

I. [±]2,t-Hydroxymethyl-4,t-[9-adenyl]-6,8-dioxa-7-ethoxy-cis-bicyclo[3.3.0]octane A solution of 950 mg of the [±]2,t-hydroxymethyl-4,t-[6-chloro-9H-purin-9-yl]-6,8-dioxa-7-ethoxy-cis-bicyclo[3.3.0]-octane prepared in Part H in 10 mL of liquid NH₃ and 40 mL of methanol was heated in a stainless steel bomb at 60° for 16 hours. Removal of the solvent gave 1.23 g of [±]2,t-hydroxymethyl-4,t-[9-adenyl]-6,8-dioxa-7-ethoxycis-bicyclo[3.3.0]-octane.

J. 1,t-9-Adenyl)-2,c-3,c-dihydroxy-4,t-[2-thia-3-(2-aminoethyl)-8-aminooctyl]cyclopentane hydrochloride

[±]2,t-hydroxymethyl-4,t-[9-adenyl]-6,8-dioxa-7-ethoxy-cis-bicyclo[3.3.0]octane prepared in Part I was converted to 1,t-(9-adenyl)-2,c-3,c-dihydroxy-4,t-[2-thia-3-(2-aminoethyl)-8-aminooctyl]cyclopentane hydrochloride according to a procedure similar to that described in Example 2, Parts K and L.

K. Activity of 1,t-9-Adenyl)-2,c-3,c-dihydroxy-4,t[2-thia-3-(2-aminoethyl)-8-aminooctyl]cyclopentane hydrochloride Interferon potentiating activity and spermidine synthase inhibiting activity of the 1,t-adenyl-2,c-3,c-dihydroxy-4,t[2-thia-3-(2-aminoethyl)-8-aminooctyl]cyclopentane prepared in the Example were determined according to the General Procedures described above.

The challenge virus was vesicular stomatitis virus [VSV], New Jersey strain. Activity was assayed on Maden-Darby bovine kidney cells in monolayer cultures. It was determined that a concentration of 50 μg/ml of the title compound gave a 2× potentiation of human alpha [leucocyte] interferon. The compound by itself showed no antiviral activity against VSV.

Spermidine synthase inhibiting activity of the t-adenyl-2,c-3,c-dihydroxy-4,t-[2-thia-3-(2-aminoethyl)-8-aminooctyl]cyclopentane prepared in this Example was determined according to the General Procedures described above. It was found that 0.002 mM of the specified compound was needed to effect 50% inhibition of spermidine synthase activity.

What is claimed is:

1. A compound of formula (I)

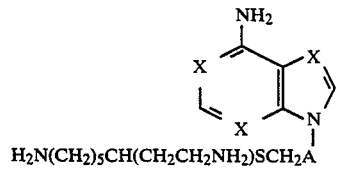

H₂N(CH₂)₅CH(CH₂CH₂NH₂)SCH₂A wherein X is N, and A is selected from the group consisting of —CH₂OCH₂—, —CH₂CHOHCHOHCH₂—, and

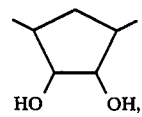

and salts thereof.

2. A compound as defined in claim 1, wherein X is N and A is —CH₂OCH₂—.
3. A compound as defined in claim 1, wherein X is N and A is —CH₂CHOHCHOHCH₂—.
4. A compound as defined in claim 1, wherein X is N and A is
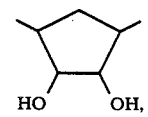
* * * * *